US00PP18838P2

(12) United States Plant Patent
Stemkens

(10) Patent No.: US PP18,838 P2
(45) Date of Patent: May 27, 2008

(54) *DIASCIA* PLANT NAMED 'DIASCLARO'

(50) Latin Name: *Diascia barberae*
Varietal Denomination: Diasclaro

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/641,413

(22) Filed: Dec. 19, 2006

(51) Int. Cl.
*A01H 5/00* (2006.01)

(52) U.S. Cl. ..... Plt./425; Plt./263.1

(58) Field of Classification Search ..... Plt./425, Plt./263

See application file for complete search history.

*Primary Examiner*—Anne Marie Grunberg
*Assistant Examiner*—S. B. McCormick-Ewoldt
(74) *Attorney, Agent, or Firm*—S. Matthew Edwards

(57) ABSTRACT

A new *Diascia* plant particularly distinguished by its rosy flowers, which produces no seeds, and has a growing habit that is spreading and hanging.

1 Drawing Sheet

Latin name of the genus and species of the plant claimed: *Diascia barberae.*
Varietal denomination: 'Diasclaro'.

BACKGROUND OF THE NEW PLANT

The present invention comprises a new distinct cultivar of *Diascia,* botanically known as *Diascia barberae.*

The new cultivar is a product resulting from the cross of 'B0015-5' and 'B0015-4.' 'B0015-5' is a rose flowering *Diascia.* 'B0015-5' is not commercially available and is not known by any synonyms. 'B0015-4' is a lilac flowering *Diascia.* 'B0015-4' is not commercially available and is not known by any synonyms. Neither 'B0015-5' nor 'B0015-4' has been patented.

As a result of this cross the present cultivar was created in 2000 in Enkhuizen, Netherlands and has been repeatedly asexually reproduced by cuttings in Enkhuizen, Netherlands and Sarrians, France over a three year period. It has been found to retain its distinctive characteristics through successive propagations. The new variety is stable and reproduces true to type in successive generations of asexual reproduction.

This new *Diascia* plant is an annual in most climatical zones in the US, only in zones 8, 9 and 10 it is a perennial plant.

DESCRIPTION OF THE DRAWING

This new *Diascia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Diascia.* The data which defines these characteristics were collected from asexual reproductions carried out in Enkhuizen, Netherlands. The plant history was taken on 10 week old plants, cultured in 10.5 cm containers, and blossomed under natural light in a greenhouse.

Color readings were taken in the greenhouse under ambient light. Color references are primarily to the R.H.S. Colour Chart of The Royal Horticultural Society of London.

TABLE 1

DIFFERENCES BETWEEN THE NEW CULTIVAR 'DIASCLARO', ITS PARENTS AND A SIMILAR CULTIVAR

| | 'Diasclaro' | 'B0015-5' | 'B0015-4' | 'Diastu' (U.S. Plant Patent No. 13,949) |
|---|---|---|---|---|
| Flower color | Rose | Rose | Pink | Antique Rose |
| Plant size | Medium | Medium | Small | Medium |
| Leaf size | Medium | Medium | Large | Medium |
| Internodes | Medium | Short | Short | Short |

The plant:

*Classification.*—Botanical: *Diascia barberae.*

*Parentage.*—Female parent: A seedling named 'B0015-5' is one of our seedlings from our B-generation of plants bred in 1996. Pollen parent: A seedling named 'B0015-4' is one of our seedlings from our B-generation of plants bred in 1996.

*Growth habit.*—Spreading, ascending.

*Plant height.*—22-32 cm.

*Spreading area of plant.*—26-42 cm.

*Growth rate.*—Vigorous.

*Strength.*—Very good.

*Branching character.*—Freely branching and lateral branching at every node.

*Quantity of branches.*—80-100 branches per plant.

*Blooming period.*—From April until November.

The stem:

*Diameter.*—1.2 mm.

*Shape.*—Round.

*Length.*—15-18 cm.

*Color.*—141A.

*Anthocyanin pigmentation.*—Absent.

*Length of internode.*—Vegetative growth: 14-18 mm. Generative growth: 15-35 mm.
*Pubescence.*—Not pubescent.

The foliage:
*Phyllotaxis.*—Opposite, decussate.
*Number of leaves per lateral stem.*—22-32.
*Shape of blade.*—Cordate.
*Texture.*—Upper side: Smooth, glossy. Lower side: Smooth.
*Attachment to leaf.*—Petiolate.
*Venation.*—Pinnate.
*Color of veins.*—Upper side: 138B. Lower side: 138D.
*Leaf margin.*—Dentate.
*Leaf base.*—Cordate.
*Leaf apex.*—Abruptly acute.
*Length.*—24-38 mm.
*Width.*—20-34 mm.
*Depth of incision.*—Less than 1 mm.
*Color.*—Upper side: 138C. Lower side: 137C.
*Pubescence.*—No pubescence.
*Length of petiole.*—2 mm.
*Diameter of petiole.*—1-2 mm.
*Color of petiole.*—138C.
*Petiole surface texture.*—Smooth, glossy.

The bud:
*Peduncle length.*—18-28 mm, depending on season.
*Peduncle width.*—1-2 mm.
*Peduncle shape.*—Long and threadlike.
*Peduncle color.*—137B.
*Size of the bud.*—Length: 2 mm. Diameter: 2 mm.
*Shape of the bud.*—Oval.
*Color of the bud.*—157B.
*Number of buds per lateral branch.*—14-24.
*Sepals.*—Color both surfaces: 141A. Form: Star-shaped. Number: 5, parted. Length: 1-2 mm. Width: 1-2 mm. Shape: Elliptic, apex acute, base truncate. Margin: Entire. Texture: Smooth.
*Bracts.*—Color upper side: 141A. Color lower side: 141B. Arrangement: Sessile. Number: One underneath every pedicel. Length: 1-2 mm. Width: 1-2 mm. Apex: Acute. Base: Subcordate. Margin: Entire. Texture: Smooth.
*Pedicels.*—Color: 141C. Shape: Threadlike. Length: 6-8 mm. Diameter: 1 mm.

The flower:
*Inflorescence length.*—6-10 cm.
*Inflorescence diameter.*—2-4 cm.
*Flower width.*—18-24 mm.
*Flower length.*—17-20 mm.
*Flower depth.*—6-9 mm.
*Flower aspect.*—Tipped upward and outward.
*Borne.*—Solitary, on axillary racemes.
*Form.*—Zygomorphic, five lobed, double nectar spur.
*Cluster.*—Raceme.
*Color.*—Upper surface: 73A, bit lighter, on the two upper banner petals there is a small yellow (color 9C) indentation just above the reproductive organs. Lower surface: 68D, on the two upper banner petals there is a small light yellow (color 9D) indentation at the base.
*Overlapping of the petals.*—Separate.
*Number of petals.*—Five: two upper banner petals, two lateral petals and one larger basal lip petal.
*Shape of the banner petals.*—Apex rounded, base fused.
*Shape of the lateral petals.*—Apex rounded, base fused, lower surface modified into nectar spurs.
*Shape of the basal lip petal.*—Apex truncate, base fused.
*Petal margin.*—Entire.
*Petal surface texture.*—Smooth.
*Size of the banner petals.*—Length: 4-6 mm. Width: 4-8 mm.
*Size of the lateral petals.*—Length: 4-6 mm. Width: 4-8 mm.
*Size of the basal lip petal.*—Length: 18-22 mm. Width: 20-24 mm.
*Spur.*—Length: 8 mm. Diameter: 1-2 mm at petal attachment. Color: 63A.
*Number of flowers per raceme.*—25-35.
*Fragrance.*—No fragrance.
*Lastingness of the bloom.*—New florets continue to open in one raceme over a period of 14 days.
*Lastingness of one flower.*—About 3 days depending on temperature.
*Flowering season.*—Depending on climate from March until December.

The reproductive organs:
*Androecium.*—Stamen number: Three. Anther shape: Two-lobed. Anther size: Less than 1 mm. Anther color: 7A. Amount of pollen: Very much pollen. Pollen color: 7A.
*Gynoecium.*—Pistil number: 1. Stigma shape: Rounded. Pistil length: 2-3 mm. Style length: 1-2 mm. Style color: 143A. Stigma color: 157B. Ovary color: 134B.

The fruit and the seed: No fruit development or seedset has been observed to date.

The roots:
*Type of roots.*—Fibrous.
*Rooting habit.*—Fine and freely branching.
*Color.*—Whitish, N155B.

Physiological and ecological characteristics:
*Disease/pest resistance.*—Plants of the new *Diascia* have not been noted to be resistant to pathogens or pests common to *Diascia.*
*Temperature tolerance.*—Plants of the new *Diascia* have been observed to tolerate temperatures from −2 to 35 degrees C.

What is claimed is:

1. A new and distinct variety of *Diascia* plant named 'Diasclaro,' as substantially illustrated and described herein.

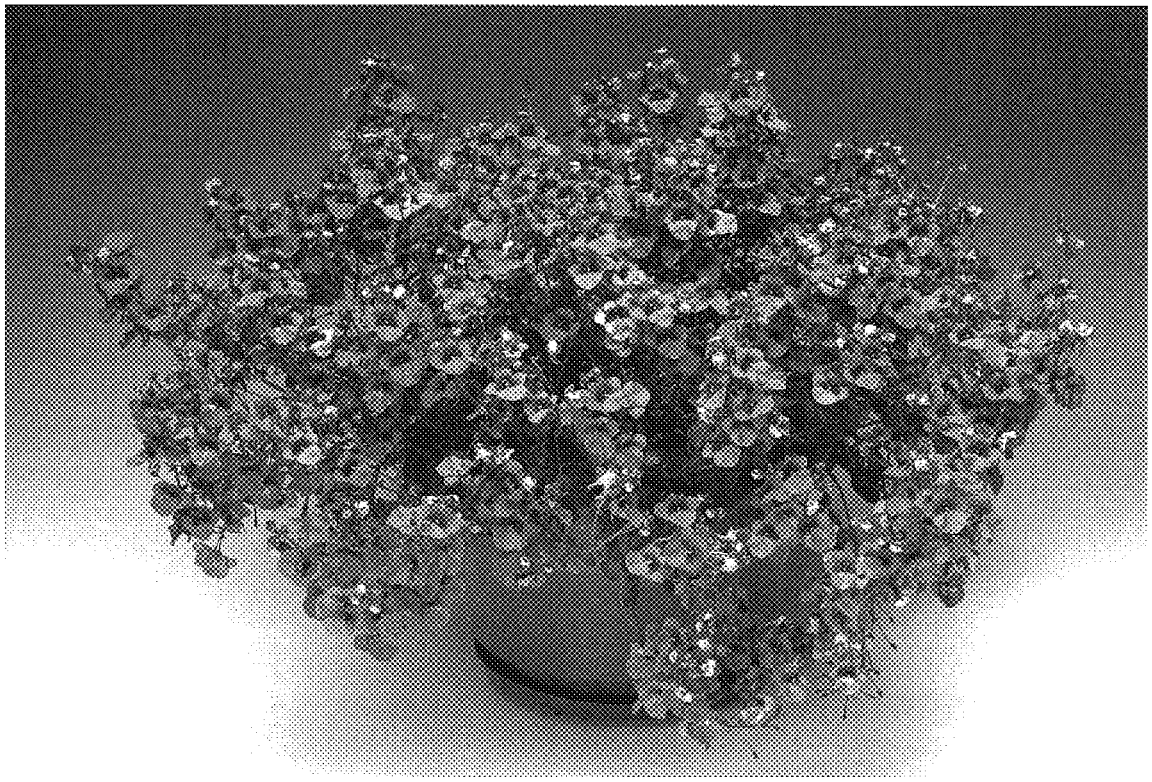

* * * * *